(12) United States Patent
Witschen

(10) Patent No.: US 8,448,907 B2
(45) Date of Patent: May 28, 2013

(54) MEDICAL TRAY HAVING TELESCOPING LEG

(76) Inventor: Laura Witschen, Aurora, MI (US)

( * ) Notice: Subject to any disclaimer, the term of this patent is extended or adjusted under 35 U.S.C. 154(b) by 112 days.

(21) Appl. No.: 13/038,531

(22) Filed: Mar. 2, 2011

(65) Prior Publication Data

US 2012/0223037 A1 Sep. 6, 2012

(51) Int. Cl.
*A47J 47/16* (2006.01)
*A47B 9/20* (2006.01)
*F16M 13/00* (2006.01)

(52) U.S. Cl.
USPC ............ 248/145.6; 248/188.5; 248/523; 108/147.19; 109/51; 135/24

(58) Field of Classification Search
USPC .......... 248/132, 145.6, 151, 157, 161, 176.1, 248/188, 188.5, 188.2, 188.91, 439, 450, 248/460, 523, 524, 522; 5/83.1, 510, 600, 5/658, 626, 662; 206/564, 370, 549.1, 459.1, 206/315.11, 315.5, 581; 108/147.19, 147.21, 108/144.11, 146; 109/50, 51, 52; 135/16, 135/24, 25.4
See application file for complete search history.

(56) References Cited

U.S. PATENT DOCUMENTS

| | | | | |
|---|---|---|---|---|
| 3,031,247 A * | 4/1962 | Schieve | ................... | 248/188.91 |
| 5,199,361 A * | 4/1993 | Robinson | ................... | 109/51 |
| 5,570,483 A * | 11/1996 | Williamson | ................... | 5/83.1 |
| 5,577,611 A * | 11/1996 | Greenall | ................... | 206/459.1 |
| 7,421,956 B1 * | 9/2008 | McCarthy et al. | ................ | 108/25 |
| 8,056,162 B2 * | 11/2011 | Newkirk et al. | ................. | 5/510 |
| 8,240,755 B2 * | 8/2012 | Valaei Khiabani | ........ | 297/159.1 |
| 2011/0166891 A1 * | 7/2011 | Zerhusen et al. | ................ | 705/3 |

FOREIGN PATENT DOCUMENTS

FR 2841763 * 9/2004
FR 2908613 * 5/2008

* cited by examiner

*Primary Examiner* — Tan Le
(74) *Attorney, Agent, or Firm* — Arnold de Guzman

(57) ABSTRACT

A medical tray having a telescoping leg that selectively telescopes in to be out of the way so as to enable the medical tray to be placed on a flat supporting surface or stored, or that telescopes out to provide a secure and stable support that places the medical tray contents in an elevated position. The telescoping of the telescoping leg is controlled by a one hand operated, dual action release mechanism.

20 Claims, 4 Drawing Sheets

MEDICAL TRAY HAVING TELESCOPING LEG

FIELD OF THE INVENTION

The present invention relates to medical trays. More specifically, the present invention relates to medical trays having telescoping legs that selectively telescope in so as to be out of the way or that telescope out to provide a stable, elevated support.

BACKGROUND OF THE INVENTION

When providing medical care or services in a hospital setting it is very common for a medical professional to carry needed supplies in a medical tray to a patient. For example, nurses starting I.V.s or doing point of care testing or phlebotomists taking blood will often carry needles, blood collection tubes, biohazardous waste containers and other items to a patient's bedside in a medical tray that retains such items in a basket.

Medical trays used in a hospital setting are often relatively specialized items tailored to the particular service being performed. For example, a phlebotomist's tray generally has basket with high sides to prevent content spilling, a central handle for carrying the tray, and internal ribs that not only provide mechanical strength but also retain various items such as needles in a specific position.

While generally successful, prior art medical trays have at least one major drawback. To use, they must first be placed on a surface such as a patient's bed, bed stand, or bedside table. These items are often contaminated with various bodily fluids and possibly by communicable bacteria or viruses. Thus, simply placing a medical tray on a surface near a patient to perform a service may result in transmission of pathogens causing nosocomial infections.

Since the foregoing problem is well-known, hospitals sometimes require medical service providers to use mobile carts to support their medical trays. While this may address the specific problem of reducing the transmission of pathogens, it creates several issues. First, mobile carts are not readily moveable up and down stairs. This forces a medical provider to use elevators to move from one floor to another. In turn, that can dramatically slow down the providing of medical services, particularly when one or more elevators are out of service, overused, or simply slow. Mobile carts are also difficult to maneuver around patient tables and I.V. stands, and hospital rooms are sometimes cluttered.

Therefore, medical trays having support legs would be beneficial. Even more beneficial would be medical trays having support legs that selectively telescope in to be out of the way to allow the medical tray to be placed on a medical cart or other surface and for storage, and that selectively telescope out to provide elevated, stable supporting platforms. Even more beneficial would be medical trays having telescoping legs that telescope in and out and that further incorporate a one-handed release mechanism that selectively enables telescoped-in legs to telescope out to provide elevated, stable supporting platforms.

BRIEF SUMMARY OF THE INVENTION

The principles of the present invention provide for medical trays having telescoping legs that selectively telescope in and out. Those principles are implemented in a medical tray having a telescoping leg that selectively telescopes in to be out of the way to allow the medical tray to be placed on a medical cart or other surface and for storage, while also selectively telescoping out to provide an elevated, secure and stable support. Preferably a telescoped-in leg is released using a one hand operated, dual action release mechanism.

A medical tray in accord with the principles of the present invention includes a basket having a carrying handle assembly, a plurality of sidewalls and a bottom wall. The sidewalls and bottom wall define an interior region for retaining supplies and a lower region. The carrying handle assembly includes a body that extends upward from the bottom wall and out of the interior region, a handle for enabling easy carrying of the medical tray, and a one-hand operated, dual action release mechanism. A telescoping leg comprised of a plurality of telescoping tubes attaches to the medical tray by passing through the bottom wall and into the body. When fully telescoped-in the telescoping leg does not extend out of the lower region.

The release mechanism retains the telescoping leg in its fully telescoped-in position until the telescoping leg is released. When the telescoping leg is fully telescoped-in the medical tray can sit unobstructed on a medical cart or other flat surface and for is suitable for easy storage. When the release mechanism releases the telescoping leg at least one telescoping tube drops down such that a portion of the telescoping leg extends out of the lower region. Spring loaded pins selectively lock the telescoping tubes in position. The release mechanism beneficially includes a grip for applying a release force that releases the telescoped-in telescoping leg and a release slide for selectively preventing the grip from applying the release force until desired. Beneficially, the release mechanism can be operated using one hand. Also beneficially, the bottom of the telescoping leg includes a plurality of support legs for providing lateral stability.

BRIEF DESCRIPTION OF THE DRAWINGS

The advantages and features of the present invention will become better understood with reference to the following detailed description and claims when they are taken in conjunction with the accompanying drawings, in which like elements are identified with like symbols, and in which:

FIG. 3 is a side perspective view of the medical tray shown in FIG. 1 wherein the telescoping leg 12 is fully telescoped-in.

DETAILED DESCRIPTION OF THE INVENTION

The presently disclosed subject matter will now be described more fully hereinafter with reference to the accompanying drawings in which an embodiment of the present invention is shown. However, it should be understood that this invention may take different forms and thus should not be construed as being limited to the specific embodiment set forth herein. In the figures like numbers refer to like elements throughout.

Figure 1:
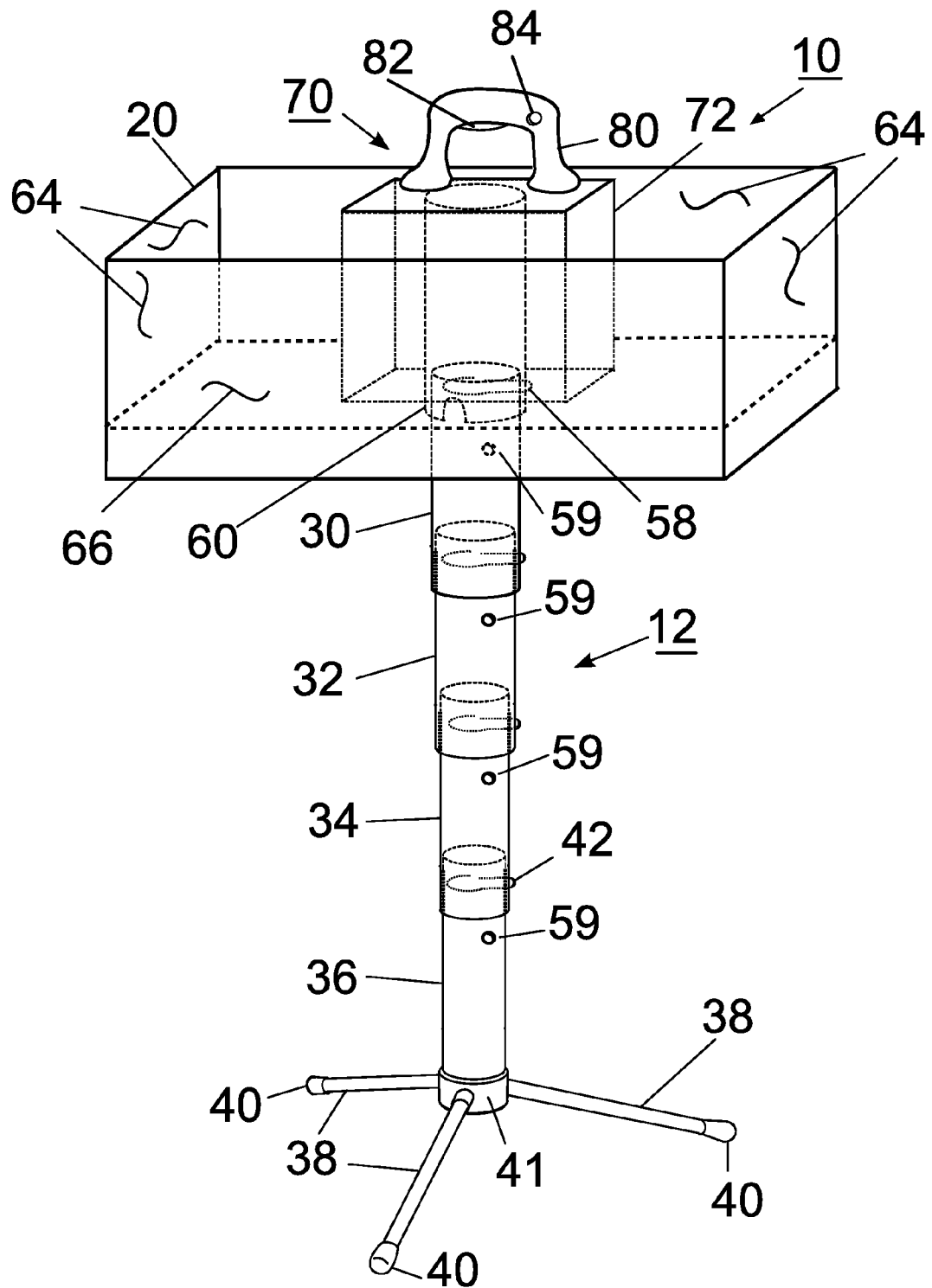
FIG. 1 is a simplified perspective view of a medical tray according to a first embodiment of the present invention wherein a telescoping leg is fully extended.

FIG. 1 illustrates an embodiment of a medical tray 10 that is in accord with the principles of the present invention. As shown, the medical tray 10 has a telescoping leg 12 that can telescope out of a basket 20. As shown, the telescoping leg 12 is comprised of an upper tube 30, an upper middle tube 32, a lower middle tube 34, a lower tube 36, and at least three feet 38 that terminate in pads 40. Those feet 38 extend from a clamp 41 that is attached to the end of the lower tube 36. The tubes 30, 32, 34, and 36 are configured to very closely telescope inside one another so that they can extend to support the basket 20 at a useful height.

When the telescoping leg 12 is fully telescoped out it is important that the telescoping leg 12 provides both lateral stability and vertical support for the basket 20. That goal is to some extent provided by features shown in FIG. 2 (which is a partial cut-away view of portions of the telescoping leg 12 without the feet 38 or the clamp 41). As shown, when the telescoping leg 12 is fully extended its lower tube 36 closely fits inside the mating lower middle tube 34 and is retained far enough inside the lower middle tube 34 that the walls of the lower tube 36 and the lower middle tube 34 provide lateral support. A close fit will be required to provide the desired overall stability. The lower tube 36 is retained in its fully extended position by a spring pin 42 that fits into a hole 44 through the lower middle tube 34. The mating of the spring pin 42 and the hole 44 prevents the lower tube 36 from sliding out of the lower middle tube 34 and also prevents the lower tube 36 from sliding back into the lower middle tube 34.

Figure 2:
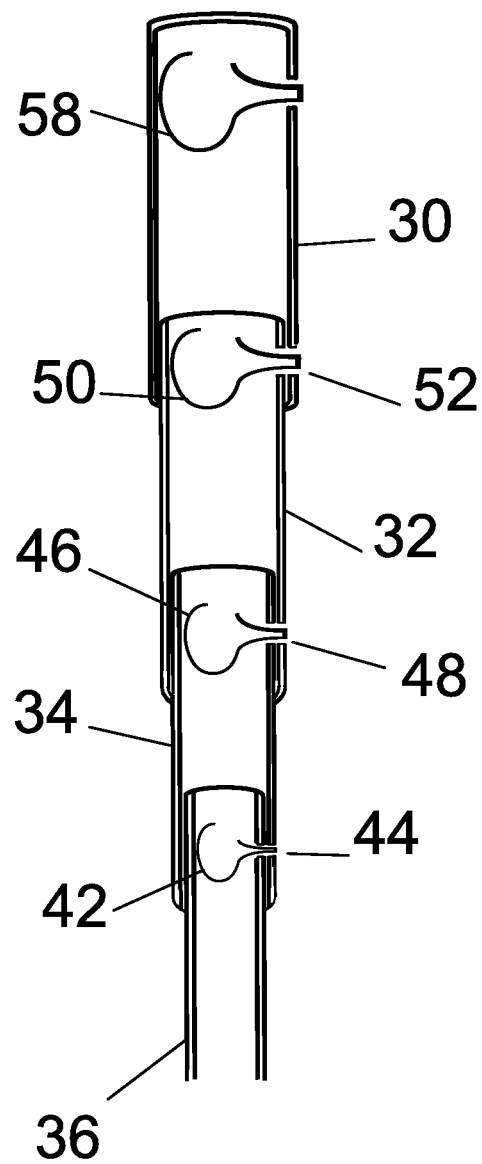
FIG. 2 is a partial cut-away view of the telescoping leg 12 shown in FIG. 1.

Still referring to FIG. 2, when the telescoping leg 12 is fully extended its lower middle tube 34 extends out of the mating upper middle tube 32 but is retained inside the upper tube middle 32 far enough that the walls of those tubes provide lateral support. The lower middle tube 34 is retained in its extended position by a spring pin 46 that fits into a hole 48 through the upper middle tube 32. The mating of the spring pin 46 in the hole 48 prevents the lower middle tube 34 from sliding out of the upper middle tube 32 when the telescoping leg 12 is fully extended and also prevents the lower middle tube 34 from sliding back into the upper middle tube 32. Likewise, when the telescoping leg 12 is fully extended its upper middle tube 32 extends out of the mating upper tube 30 but is retained inside the upper tube 30 far enough that the walls of those tubes provide lateral support. The upper middle tube 32 is retained in its extended position by a spring pin 50 that fits into a hole 52 through the upper tube 30. The mating of the spring pin 50 and the hole 52 prevents the upper middle tube 32 from sliding out of the upper tube 30 when the leg is fully extended and also prevents the upper middle tube 32 from sliding back into the upper tube 30. Still referring to FIG. 2, the telescoping leg 12 further includes a spring pin 58 that springs into a hole in the basket 20 as shown in FIG. 1.

When its is desirable that the telescoping leg 12 be fully telescoped-in, this is accomplished by pushing spring pin 42 into the hole 44, which allows the lower tube 36 to slide into the lower middle tube 34, by pushing the spring pin 46 through the hole 48, which allows the lower middle tube 34 and the lower tube 36 to slide into the upper middle tube 34, and by pushing the spring pin 50 through the hole 52, which allows the upper middle tube 32, the lower middle tube 34, and the lower tube 30 to slide into the upper tube 30. Likewise, when the spring pin 56 is pushed through its hole 58 all of the telescoping tubes collapse into an aperture 60 in the basket 20 (see FIG. 1, FIG. 3, FIG. 4, and reference the discussion that follows).

Figure 3:
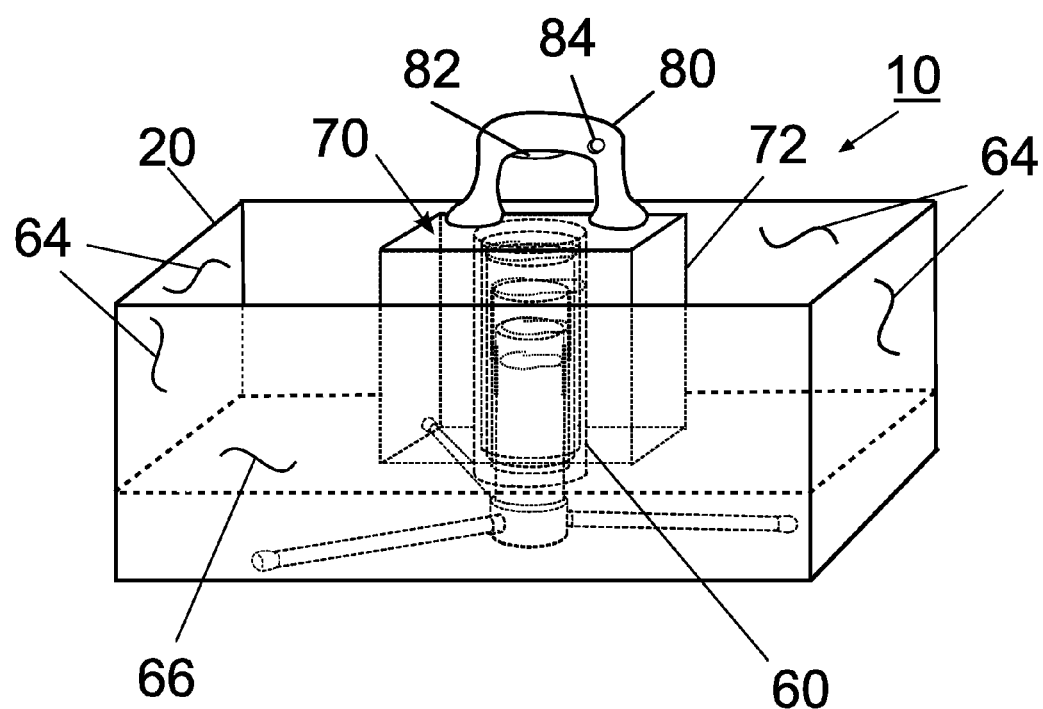

Turning now to FIGS. 1 and 3, the shape of the basket 20 is defined primarily by the sidewalls 64 and by the bottom wall 66. The bottom wall 66 effectively divides the basket 20 into two regions: above the bottom wall 66 is a region referred to hereinafter as the upper volume while below the bottom wall 66 is a region referred to hereinafter as the lower volume. As best shown in FIG. 3, the sidewalls 64 extend below the bottom wall 66 enough to provide a large enough lower volume to fully retain all of the telescoping leg 12, including the feet 38 and pads 40, when that leg is fully telescoped-in. This provides a flat bottom surface defined by the bottoms of the sidewalls 64 which enables the medical tray 10 to sit unobstructed on a flat surface such as a medical cart while also enabling easy storage.

Figure 4:
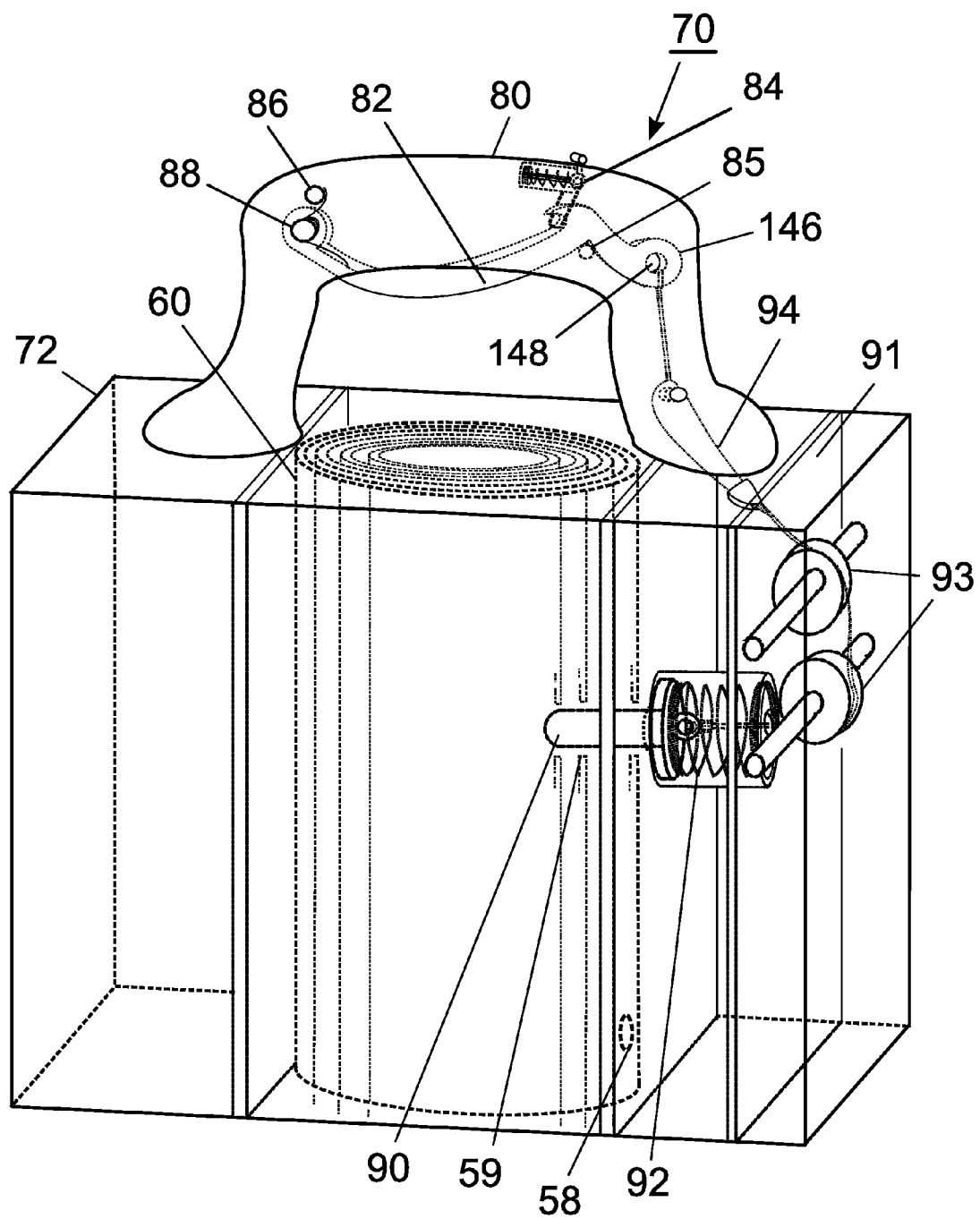
FIG. 4 is a partial sectional view of the handle assembly 80 shown in FIGS. 1 and 3.

Referring now to FIGS. 1, 3, and 4, the basket 20 also includes a handle assembly 70. The handle assembly 70 includes a body 72 that includes the aperture 60 (best shown in FIGS. 1 and 4) and the hole for the spring pin 58. Thus when the telescoping leg 12 is fully telescoped-in the various telescoping tubes 30, 32, 34, and 36 slide into the aperture 60 of the handle assembly 70. The handle assembly 70 also includes a carrying handle 80, a grip 82 and a thumb release 84.

FIG. 4 illustrates the handle assembly 70 in more detail. As shown therein, a pin 90 extends through a wall 91 of the handle assembly 70 and through a plurality of aligned apertures 59, each of which is defined through a different one of the telescoping tubes 30, 32, 34, and 36 (also see FIG. 1). Those apertures 59 are located in their individual tubes such that when the telescoping leg 12 is fully telescoped-in the apertures 59 align such that the pin 90 can pass through all of them, thereby locking the telescoping tubes 30, 32, 34, and 36 within the aperture 60. To maintain the telescoping tubes in position the pin 90 is biased into the aligned apertures 59 by a spring 92. The pin 90 also connects to a release cable 94 that passes over one or more rollers 93. A release force applied to the release cable 94 pulls the pin 91 out of the aligned apertures 59 (but not out of the wall 91). This releases the telescoping tubes 30, 32, 34, and 36. Gravity drops those tubes drop to cause the telescoping leg 12 to assume the fully telescoped-out position shown in FIG. 1.

FIG. 4 also illustrates how a release force can be applied to the release cable 94. As shown, the handle 80 includes an internal pivot pin 88. Mounted on the pivot pin 88 is the multiply-curved grip 82 which partially extends out of the bottom of the handle 80 and then passes back into the handle 80. The grip 82 includes an end 146 that is opposite the end that connects to the pivot pin 88. The end 146 has an aperture 148. Attached to that aperture 148 is the release cable 94 which, as noted, runs to the pin 90.

Still referring to FIG. 4, the handle 80 further includes a spring 86 that biases the grip 82 so as to rotate the end 146 downward and into a stop pin 85. The stop pin 85 limits the downward motion of the grip 82. Above the stop pin 85 and grip 82 is a thumb actuated, spring loaded release slide 84. When the release slide 84 is not actuated it sits over the grip 82 and allows a user to grab the handle 80 and grip 82 and to carry the medical tray 10 without releasing the telescoping leg 12. However, when the release slide 84 is moved toward the left the release 84 clears the grip 82 which allows the grip 82 to move upward and thus to release the telescoping leg 12 via the cable 94.

As described herein the medical tray 10 requires two steps to release the telescoping leg 12. Beneficially both of those steps can be performed using one hand. First, the release slide 84 is slid off the top of the grip 82. At the same time the grip 82 is moved into the handle 80, which creates the release force. After release, the spring 86 moves the grip 82 down to the stop 85 and the spring load on the release slide 84 moves the release slide 84 back over the top of the grip 82.

From the foregoing it is obvious that the telescoping leg 12 can be collapsed into a compact condition to facilitate easy storage, transportation, and use. It also can be extended so as to to position the basket 20 in an elevated position to assist a user.

It is to be understood that while the figures and the above description illustrate the present invention, they are exemplary only. They are not intended to be exhaustive or to limit the invention to the precise forms disclosed, and obviously many modifications and variations are possible in light of the above teaching. Others who are skilled in the applicable arts will recognize numerous modifications and adaptations of the illustrated embodiments that remain within the principles of the present invention. Therefore, the present invention is to be limited only by the appended claims.

What is claimed:

1. A medical tray, comprising:
    a basket having a handle assembly comprised of a carrying handle and a base with an elongated aperture in said basket, said basket further having a plurality of sidewalls, each having a top and a bottom, and a bottom wall disposed between said tops and bottoms so as to define an upper volume between said sidewall tops and said bottom wall and a lower volume defined between said sidewall bottoms and said bottom wall;
    a telescoping leg comprised of a plurality of closely fitting telescope tubes that can slide relative to one another and to said elongated aperture;
    means to retain said telescoping leg within said elongated aperture until released by a release force;
    a release mechanism within said handle assembly for producing said release force, said release mechanism including a grip for creating a release force and a release member for selectively preventing said grip from applying said release force to said retain means;
    wherein said release member is on said carrying handle;
    wherein said release member sits over said grip as said release member prevents said grip from applying said release force to said retain means so that said telescoping leg is retained within said elongated aperture;
    wherein said release member clears said grip as said release member allows said grip to move and to apply said release force to said retain means so that said release force allows the telescoping leg to slide out of said elongated aperture; and
    wherein a user can operate said release member to allow said grip to apply said release force to said retain means.

2. The medical tray according to claim 1 wherein said release mechanism can be released using one hand.

3. The medical tray according to claim 1 wherein said telescoping leg further includes a clamp attached to said telescoping leg and at least three feet that extend from said clamp.

4. The medical tray according to claim 3 wherein each foot includes a pad.

5. The medical tray according to claim 1 wherein said release mechanism includes a mechanical stop that limits the motion of said grip and a bias member that biases said grip toward said stop.

6. The medical tray according to claim 1 further comprising a spring, said spring biases said retain means so that said retain means locks one telescopic tube in another telescopic tube within said elongated aperture.

7. The medical tray according to claim 1 wherein said basket is configured to hold medical supplies.

8. The medical tray according to claim 1 wherein said feet are retained in said lower volume when said telescoping leg is retained within said elongated aperture.

9. The medical tray according to claim 1, further comprising:
    a plurality of spring pins, each telescoping tube including a respective spring pin among the plurality of spring pins; and
    wherein at least some of said plurality of spring pins fit into respective holes in at least some of said telescoping tubes as said telescoping leg is fully extended; and
    wherein one of said spring pins fits into a respective hole in said basket as said telescoping leg is fully extended.

10. The medical tray according to claim 1, wherein said sidewall bottoms define a flat bottom surface as said telescoping leg is retained within said elongated aperture.

11. A medical tray, comprising:
    a basket having a handle assembly comprised of a carrying handle and a base with an elongated aperture in said basket, said basket further having a plurality of sidewalls, each having a top and a bottom, and a bottom wall disposed between said tops and bottoms so as to define an upper volume between said sidewall tops and said bottom wall and a lower volume defined between said sidewall bottoms and said bottom wall;
    a telescoping leg comprised of a plurality of closely fitting telescope tubes that can slide relative to one another and to said elongated aperture;
    a pin configured to retain said telescoping leg within said elongated aperture until released by a release force;
    a release mechanism within said handle assembly for producing said release force, said release mechanism including a grip for creating a release force and a release member for selectively preventing said grip from applying said release force to said pin;
    wherein said release member is on said carrying handle;
    wherein said release member sits over said grip as said release member prevents said grip from applying said release force to said pin so that said telescoping leg is retained within said elongated aperture;
    wherein said release member clears said grip as said release member allows said grip to move and to apply said release force to said pin so that said release force allows the telescoping leg to slide out of said elongated aperture; and
    wherein a user can operate said release member to allow said grip to apply said release force to said pin.

12. The medical tray according to claim 11 wherein said release mechanism can be released using one hand.

13. The medical tray according to claim 11 wherein said telescoping leg further includes a clamp attached to said telescoping leg and at least three feet that extend from said clamp.

14. The medical tray according to claim 13 wherein each foot includes a pad.

15. The medical tray according to claim 11 wherein said release mechanism includes a mechanical stop that limits the motion of said grip and a bias member that biases said grip toward said stop.

16. The medical tray according to claim 11 further comprising a spring, said spring biases said pin so that said pin locks one telescopic tube in another telescopic tube within said elongated aperture.

17. The medical tray according to claim 11 wherein said basket is configured to hold medical supplies.

18. The medical tray according to claim 11 wherein said feet are retained in said lower volume when said telescoping leg is retained within said elongated aperture.

19. The medical tray according to claim 11, further comprising:

a plurality of spring pins, each telescoping tube including a respective spring pin among the plurality of spring pins; and wherein at least some of said plurality of spring pins fit into respective holes in at least some of said telescoping tubes as said telescoping leg is fully extended; and wherein one of said spring pins fits into a respective hole in said basket as said telescoping leg is fully extended.

20. The medical tray according to claim 11, wherein said sidewall bottoms define a flat bottom surface as said telescoping leg is retained within said elongated aperture.

* * * * *